(12) United States Patent (10) Patent No.: US 7,006,347 B1
Kroll et al. (45) Date of Patent: Feb. 28, 2006

(54) LOW DEFORMATION ELECTROLYTIC CAPACITOR

(75) Inventors: Mark W. Kroll, Simi Valley, CA (US); Thomas F. Strange, Easley, SC (US)

(73) Assignee: Pacesetter, Inc., Sylmar, CA (US)

( * ) Notice: Subject to any disclaimer, the term of this patent is extended or adjusted under 35 U.S.C. 154(b) by 71 days.

(21) Appl. No.: 10/917,796

(22) Filed: Aug. 12, 2004

(51) Int. Cl.
*H01G 9/00* (2006.01)
*H01G 9/04* (2006.01)
*A61N 1/18* (2006.01)

(52) U.S. Cl. .......................... 361/503; 361/508; 607/5
(58) Field of Classification Search .................. 607/5; 361/503, 508–513, 516, 517–520, 528–530
See application file for complete search history.

(56) References Cited

U.S. PATENT DOCUMENTS

| | | | |
|---|---|---|---|
| 4,518,471 A | 5/1985 | Arora | 204/129.1 |
| 4,525,249 A | 6/1985 | Arora | 204/129.75 |
| 4,760,494 A * | 7/1988 | Crum | 361/272 |
| 5,131,388 A | 7/1992 | Pless et al. | 128/419 D |
| 5,458,619 A | 10/1995 | Olson | 607/4 |
| 5,522,851 A | 6/1996 | Fayram | 607/5 |
| 6,099,600 A * | 8/2000 | Yan et al. | 29/25.03 |
| 6,118,652 A * | 9/2000 | Casby et al. | 361/517 |
| 6,249,423 B1 * | 6/2001 | O'Phelan et al. | 361/502 |
| 6,673,436 B1 * | 1/2004 | Fujimori et al. | 428/330 |

FOREIGN PATENT DOCUMENTS

| | | | |
|---|---|---|---|
| JP | 55-158621 | * | 12/1980 |
| JP | 3-201524 | * | 9/1991 |
| WO | WO 01-16971 A1 | * | 3/2001 |

\* cited by examiner

*Primary Examiner*—Eric W. Thomas

(57) ABSTRACT

The present invention relates to electrolytic capacitors and, more particularly, to the reduction of water content within an electrolytic capacitor. Aluminum electrolytic capacitors tend to degrade with time. This is due, in part, to water in the electrolyte attacking the thin film of aluminum oxide ($Al_2O_3$) formed on the anode surface. Deformation of the aluminum oxide increases the leakage current of the capacitor, such that when one or more capacitors are used for shock delivery in an ICD, the first shock (after a hiatus) will have a significantly longer charge time. Unfortunately, one cannot remove all of the water from the electrolyte, as it is needed for conduction, as well as for the formation of the cut edges of the aluminum foil after assembly. According to the present invention, a desiccant material is used within an electrolytic capacitor casing to reduce the water content of a finished capacitor to below 1% by weight of the electrolyte. In a further embodiment, a moisture barrier layer is applied over the desiccant material, such that the desiccant material slowly absorbs moisture from the electrolyte, allowing for aging of the capacitor after assembly.

23 Claims, 4 Drawing Sheets

LOW DEFORMATION ELECTROLYTIC CAPACITOR

FIELD OF THE INVENTION

The present invention relates to electrolytic capacitors and, more particularly, to the reduction of water content within an electrolytic capacitor casing to reduce degradation of the capacitor over time.

BACKGROUND OF THE INVENTION

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

An ICD is a medical device that is implanted in a patient to monitor electrical activity of the heart and to deliver appropriate electrical and/or drug therapy, as required. ICDs include, for example, pacemakers, cardioverters and defibrillators. The term "implantable cardioverter defibrillator" or simply "ICD" is used herein to refer to any implantable cardiac device.

An ICD may be programmed to sense a tachyarrhythmia and to deliver an escalating series of pulse therapies in an effort to correct this arrhythmia. For example, U.S. Pat. No. 5,458,619 to Olson shows a device that begins charging high voltage capacitors on detection of an arrhythmia. During the charging period, the device delivers a series of antitachycardia (ATC) pacing pulses. The number of pulses may be varied as a function of the voltage to which the capacitors are to be charged, so that more extended therapies may be available where allowed by longer charging times. After the ATC pulses, the device evaluates the heart rhythm to determine whether the tachyarrhythmia has terminated. If not, when the capacitor has charged, a high voltage cardioversion or defibrillation pulse is delivered.

ICDs, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors typically consist of a cathode electrode, an electrically conductive electrolyte and a porous anode with a dielectric oxide film formed thereon. While aluminum is the preferred metal for the anode plates, other metals such as tantalum, magnesium, titanium, niobium, zirconium and zinc may be used. A typical electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388. Conventional capacitor cases using metallic cases are generally known, such as those disclosed in U.S. Pat. No. 5,522,851 issued to Fayram.

Aluminum electrolytic capacitors tend to degrade with time. This is due, in part, to water in the electrolyte attacking the thin film of aluminum oxide ($Al_2O_3$) formed on the anode surface. Deformation of the aluminum oxide increases the leakage current of the capacitor, such that when one or more capacitors are used for shock delivery in an ICD, the first shock (after a hiatus) will have a significantly longer charge time. Unfortunately, one cannot remove all of the water from the electrolyte, as it is needed for conduction, as well as for the formation of the cut edges of the aluminum foil after assembly. Therefore, what is needed in the art is a method of reducing the water content within an electrolytic capacitor casing to reduce degradation of the capacitor over time.

SUMMARY OF THE INVENTION

The present invention relates to electrolytic capacitors and, more particularly, to the reduction of water content within an electrolytic capacitor. According to the present invention, a desiccant material is applied to the inner surface of an electrolytic capacitor housing. The desiccant material is chosen such that the water content of the finished capacitor is reduced to below 1% by weight of the electrolyte, preferably to an equilibrium water level of 0.75% by weight of the electrolyte.

An electrolytic capacitor according to the present invention comprises a housing; an anode disposed in the housing wherein a barrier oxide layer is formed on at least one surface of the anode; a cathode disposed in the housing; a separator material disposed between the anode and the cathode and impregnated with a liquid electrolyte; and a desiccant material disposed in the housing. In a preferred embodiment, about 5 mg to about 60 mg of the desiccant material is applied to the inside surface of the capacitor housing. The desiccant material is selected from the group consisting of silica gel, molecular sieve and clay.

In a further embodiment, the desiccant material is covered with a moisture barrier coating to allow for very slow operation of the desiccant. The moisture barrier layer is chosen such that sufficient water content is maintained during the aging process, to allow for the formation of the cut edges of the anode foil after assembly. During the aging process, the bare aluminum edges created by the cutting process are formed inside the capacitor after assembly through interaction with water in the electrolyte. Typically, it takes about three days for aging of a finished capacitor with a water level of 2–6% by weight of the electrolyte. The moisture barrier layer is preferably a thin layer of parylene, however, other moisture barrier materials may be employed, including epoxies, silicones, urethanes and encapsulants. Preferably, the moisture barrier layer completely covers the desiccant material.

In one embodiment, an electrolytic capacitor according to the present invention is constructed of anode and cathode layers, stacked with a paper insulator or spacer between each layer. Preferably, aluminum anode foil or other valve metal foil is employed, that has been etched and formed at voltages of 400 to 500 volts, with an effective formation voltage of 450 volts. In one embodiment, the anode layer is composed of two or more anode foils stacked together without any paper spacer, to form a high energy density anode element. The cathode layer is preferably an aluminum foil or film cathode. The anode and cathode layers are then grouped together in a parallel connection to produce sufficient capacitance for the intended function. This finished stack is inserted into a case with a geometry closely following the contour of the stack.

A barrier oxide layer is formed onto one or both surfaces of the metal anode foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in greater amount of charge leaking out of the capacitor once it has been charged.

The etched and formed anode foils are cut and the capacitor is assembled. The assembled capacitor is then vacuum-impregnated with an electrically conductive electrolyte, by placing the capacitor in contact with the electrolyte and reducing the pressure to less than 50 cm Hg.

Electrolytic capacitors according to the present invention are particularly useful in the environment of an implantable cardiac device, as would be apparent to one skilled in the art.

BRIEF DESCRIPTION OF THE DRAWINGS/FIGURES

DETAILED DESCRIPTION

The present invention relates to electrolytic capacitors and, more particularly, to the reduction of water content within an electrolytic capacitor casing to reduce degradation of the capacitor over time.

Preferred embodiments are now described. While specific configurations and arrangements are discussed, it should be understood that this is done for illustrative purposes only. A person skilled in the relevant art will recognize that other configurations and arrangements can be used without departing from the spirit and scope of the invention. It will also be apparent to a person skilled in the relevant art that this invention can be employed in a variety of other devices and applications.

Figure 1:
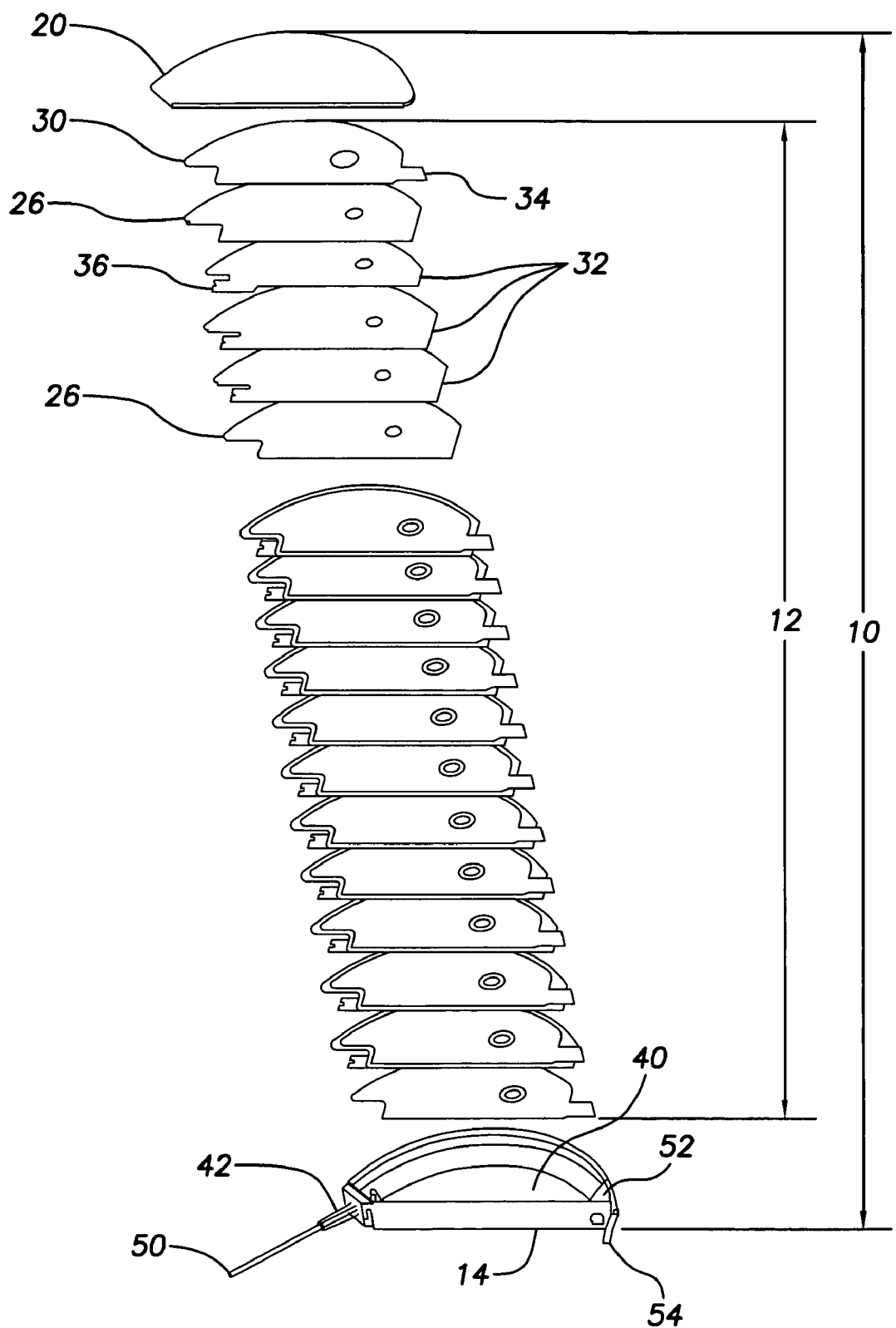
FIG. 1 shows an electrolytic capacitor having a multiple anode flat, stacked capacitor configuration according to the present invention.

In one embodiment, an electrolytic capacitor is constructed of anode and cathode layers, stacked with a paper insulator or spacer between each layer, as shown in FIG. 1. Preferably, aluminum anode foil or other valve metal foil is employed, that has been etched and formed at voltages of 400 to 500 volts, with an effective formation voltage of 450 volts. In one embodiment, the anode layer is composed of two or more anode foils stacked together without any paper spacer, to form a high energy density anode element. The cathode layer is preferably an aluminum foil or film cathode. The anode and cathode layers are then grouped together in a parallel connection to produce sufficient capacitance for the intended function. This finished stack is inserted into a case with a geometry closely following the contour of the stack, and designed to minimize the space occupied inside the finished defibrillator.

FIG. 1 illustrates a capacitor 10 having a multiple anode flat, stacked capacitor configuration 12 according to the present invention. Flat stack 12 consists of alternating conductive and separator sheets within a housing 14 enclosed by a lid 20. The sheets alternate between paper separator sheets 26, and conductive cathode sheets 30 or multiple layer anode sheets 32. In the spaces formed between adjacent separator sheets, the cathodes alternate with the multiple layer anodes. In the preferred embodiment, the dielectric is provided by an oxide layer on the etched surface of the anodes, while the cathode includes the conductive sheets, the electrolyte-saturated separator layers, and the electrolyte that fills the tunnels on the surface of the anodes. Each of the cathodes 30 has a cathode tab 34, all of which are registered with each other to be compressed together for electrical interconnection. Similarly, each of the anodes 32 has an anode tab 36, registered with each other to be compressed together for electrical interconnection. The illustration shows each anode layer having three anodes per layer for example, although according to the present invention, there may be two or more anodes per layer. Additionally, one or both of the end cathodes may be removed, with the housing itself connected to the other cathodes and functioning as a cathode.

The housing 14 is an aluminum container that defines a chamber 40 in which the stack 12 is closely received. Alternatively, the housing may be a hard plastic or titanium. The chamber has a depth equal to the thickness of the stack. The housing is provided with a feed through connector 42, which has an electrically conductive lead 50 that extends out of the housing for connection to other circuitry, with an insulative sleeve surrounding the lead and closely received in a bore defined in the wall of the housing to form an environmental seal. The anode tabs 36 are welded together and electrically connected to the terminal of feed through 42. The housing also includes a cathode attachment step 52 in its interior at a position registered with the ends of the cathode tabs 34, so that the tabs may be staked or welded as a bundle to the step for electrical connection to the housing. A cathode lead 54 is directly electrically connected to the housing for connection to the cathodes. In an embodiment in which the cathode is isolated from the housing, in which the housing is non-conductive, or in which cathodes of different groups are isolated from each other, insulated feedthroughs like those for the anodes may be used.

In an alternate embodiment of the present invention, capacitor 10 may be a traditionally-designed wound roll capacitor in either a cylindrical or flattened cylindrical shape. The anode foil in this embodiment typically has a lower capacitance per square centimeter of projected area than a flat capacitor stack design, due to the fact that the anode foil must have enough strength to be rolled. Very thin rolls of aluminum or other valve metal foil are used as the anode and cathode layers, with a separator interposed therebetween. The entire laminate is rolled up into the form of a substantially cylindrical body, or wound roll that is held together with adhesive tape and is encased, with the aid of suitable insulation, in an aluminum tube or canister. Aluminum foil is preferred for the anode layers, because of its ability to produce a sufficient quality oxide layer, its conductive properties, and its wide commercial availability. Other valve metal foils conventionally utilized in electrolytic capacitors could also be used, including titanium, tantalum, magnesium, niobium, zirconium and/or zinc. Preferably, a strip of unetched, high purity (99.99%) aluminum foil with high cubicity, wherein at least 85% of the crystalline aluminum structure is oriented in a normal position (i.e., a (1,0,0) orientation) relative to the surface of the foil, is used. Such foils are well-known in the art and are readily available from commercial sources known to those skilled in the art. In a preferred embodiment of the present invention, the anode foil may be etched in an aqueous halide based etch solution, typically a hydrochloric acid or sodium chloride solution, according to a conventional etch process; for example, U.S. Pat. No. 5,715,133 to Harrington et al. describes a suitable method of etching foil and is incorporated herein by reference in its entirety. The etch solution preferably consists of about 1.3% by weight sodium chloride, about 3.5% by weight sodium perchlorate, about 0.35% sodium persulfate, and deionized water. The etch solution preferably is heated to a temperature in the range of about 60° C. to about 95° C. The foil is etched at a DC current density of about 0.01 A/cm$^2$ to about 0.30 A/cm$^2$. A charge of about 20 coulombs/cm$^2$ to 100 coulombs/cm$^2$ is passed through the foil during the etching process, which requires an etch time in the range of about 2 minutes to about 12 minutes.

The foil is then removed from the etch solution and rinsed in deionized water. The tunnels formed during the initial etch are then widened, or enlarged, in a secondary etch solution, typically an aqueous based nitrate solution, preferably between about 1% to about 20% aluminum nitrate, more preferably between about 10% to about 14% aluminum nitrate, with less than about 1% free nitric acid. The etch tunnels are widened to an appropriate diameter by methods known to those in the art, such as that disclosed in U.S. Pat. No. 4,518,471 and U.S. Pat. No. 4,525,249, both of which are incorporated herein by reference.

After the etch tunnels have been widened, the foil is again rinsed with deionized water and dried. Finally, a barrier oxide layer is formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in greater amount of charge leaking out of the capacitor once it has been charged.

The formation process consists of applying a voltage to the foil through an electrolyte such as boric acid and water or other solutions familiar to those skilled in the art, resulting in the formation of an oxide on the surface of the anode foil. The preferred electrolyte for formation is a 100–1000 $\mu$S/cm, preferably 500 $\mu$S/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched and formed anode foils are cut and the capacitor assembled as discussed above. The pre-assembled capacitor is then vacuum-impregnated with an electrically conductive electrolyte, by placing the capacitor in contact with the electrolyte and reducing the pressure to less than 50 cm Hg. The capacitor electrolyte is typically ethylene glycol based with a straight chain dicarboxlyic acid and/or boric acid. The capacitor is held at this low pressure for 5 to 45 minutes and then pressure is restored, using the pressure to force the electrolyte mixture into the capacitor stack. The capacitor is then removed and placed in an oven at a temperature of about 65° C. to about 90(C and a maximum oxygen atmospheric concentration of 2% for a period of about 2 hours to about 24 hours. The capacitor is then aged in a normal manner by applying the working voltage to the capacitor, allowing the capacitor to reach this voltage, and then allowing the current to decrease.

Electrolytic capacitors according to the present invention are particularly useful in the environment of an implantable cardiac device, as would be apparent to one skilled in the art, as described in U.S. Pat. No. 5,522,851. Implantable cardiac devices include, for example, pacemakers, cardioverters and defibrillators. The term "implantable cardioverter defibrillator" or simply "ICD" is used herein to refer to any implantable cardiac device or implantable cardioverter defibrillator ("ICD").

Aluminum electrolytic capacitors used in medical device applications, including ICDs, have a low water content of about 2–6% by weight of the electrolyte. Water in the electrolyte is required to form the edges of the cut anodes and cathodes in the capacitor manufacturing process. During production, the anode foil is formed on one or both sides, as discussed above, but must be cut to shape. A die cut is typically used. The bare aluminum edges created by the cutting process are formed inside the capacitor after assembly through interaction with water in the electrolyte. This process is called "aging." During the aging process, a high voltage is slowly applied to form aluminum oxide on the cut edges of the aluminum anode foils. The aging process also fills breaks and cracks in the oxide layer resulting from handling during the manufacturing process. If the edges are not reformed, the capacitor will have a high leakage current, resulting in poor performance and reliability of the capacitor. Typically, it takes about three days for aging of a finished capacitor with a water level of 2–6% by weight of the electrolyte.

The finished capacitor also needs a water level of about 0.75% by weight of the electrolyte in order to maintain good conduction and have a low ESR (Equivalent Series Resistance). Thus, water concentration is necessary after assembly and sealing. However, too much water in the electrolyte can result in corrosion of the anode foil and hydrogen gas formation at the cathode that chemically attacks and degrades the aluminum anode. Free oxygen which had helped to cover defects in the oxide (after being attracted during the forming process) can diffuse into the electrolyte thus increasing the leakage current through the oxide layer. Residual water in the electrolyte may attack the oxide and form hydrides such as $Al(OH)_3$. These processes can increase the leakage current and hence increase the charge time of the capacitor. Aluminum electrolytic capacitors develop hydrogen gas at the cathode due to electrolysis. Hydrogen gas is generated by the reduction of water in the electrolyte. Exposure to conventional low water content electrolytes for more than one week will result in deformation of the oxide on the foil surface. Instability of the oxide in the liquid electrolyte results in degradation over time of the charging efficiency of the capacitor.

ICDs and other medical devices typically include capacitor maintenance software to periodically reform the aluminum oxide on aluminum electrolytic capacitors during periods of inactivity. The periodic reformation process serves to replenish the oxide and reduce the leakage current of the aluminum electrolytic capacitors. This, in turn, reduces charge time of the capacitors the first time that they are needed for therapeutic use after an extended period of non-use. The reformation process consists of charging the aluminum electrolytic capacitors to the device's maximum allowable voltage and then allowing the charge to dissipate. The capacitor is effectively repaired electrochemically during the reforming process, so that the capacitor behavior returns to normal. With the amount of residual water typical in a conventional electrolytic capacitor, the reformation process is necessary after a week to two weeks of inactivity. It is desired to push this time out to months.

Figure 2:
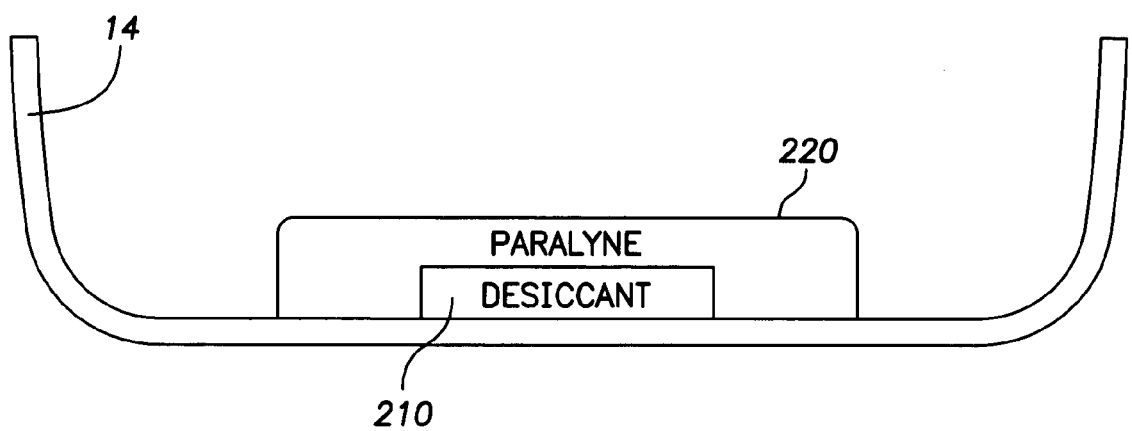
FIG. 2 is an enlarged view of a capacitor housing having a desiccant and moisture barrier layer according to the present invention.

As shown in FIG. 2, according to the present invention, a desiccant layer 210 is painted onto the inside of the can or shell 14 of the capacitor. The capacitor housing 14 is preferably an aluminum container that defines a chamber 40 in which the anode and cathode foils and electrolyte saturated separator layers are closely received. Alternatively, housing 14 may be a hard plastic or titanium. The thickness of desiccant layer 210 is chosen to reduce the water level inside the can electrolyte from an initial level of about 2% to 6% by weight of the electrolyte down to the level needed for conduction, preferably 0.75% by weight of the electrolyte at equilibrium. Desiccant layer 210 can be formed of silica gel, molecular sieve, clay and other known desiccant materials.

Typically for each gram of desiccant material, 4 grams of water are displaced. A typical electrolytic capacitor used in ICDs has approximately 1 cc of electrolyte. At a water concentration of 2–6% by weight of the electrolyte, this translates to 20–60 mg of water vapor. Accordingly, with a typical desiccant and electrolytic capacitor, 5–60 mg desiccant material is required.

However, as discussed above, a water level of about 2–6% by weight of the electrolyte is needed initially in the capacitor for the first several days in order for the aging process to work. Thus, in a more preferred embodiment, a very thin layer of parylene or other moisture barrier 220 is painted over the desiccant material. This moisture barrier layer 220 is shown in FIG. 2 not to scale. Parylene is a polymeric material produced by vapor-phase deposition and polymerization of paraxylylene. A thicker parylene barrier layer may also be used, in which a sieve pattern or the like is provided to control the surface area; such that gates are sized to allow the appropriate amount of water therethrough. Other moisture barrier materials included epoxies, silicones and urethanes. Alternatively, many other thin barriers could be used such as a "glop top" encapsulant or the like. Preferably barrier layer 220 is a spray on coating, such as would be done in generating a photoresist.

In operation, a desiccant material is painted onto the inside of the capacitor housing in a dry environment and a moisture barrier layer is then coated over the desiccant after it has dried. Preferably, the capacitor is then put in an extremely dry environment to suck all water out of the layers. Then the capacitor is assembled, as discussed above, with a water concentration of 2–6% by weight of the electrolyte. Capacitor aging is done over the next few days while the water content in the capacitor is still near its initial level. The moisture barrier layer is designed to allow the desiccant to slowly absorb moisture, such that the desiccant material cannot act for several days.

For the next days and weeks, the water in the electrolyte will be slowly brought into the desiccant to reduce the water level below 1.0% by weight of the electrolyte, preferably about 0.75% by weight of the electrolyte, at equilibrium. About this time, the capacitors are ready for assembly into an ICD. At this point, they will be charged up which will reform the edges and remove any residual damage from the high water concentration.

In an alternative embodiment, a thin strip of paper that is wet or holding moisture, can be placed along the edges of the cut capacitor, with a time release formulation or mechanism, such that water is exuded over time, such as a two day period. With a desiccant material, as discussed above, disposed in center of the capacitor housing, the desiccant will not suck up water immediately from the wet paper. According to this embodiment of the invention, while the aging process is facilitated by the thin strip of wet paper, a lower water content equilibrium can be obtained as a result of the action of the desiccant material.

Accordingly, the present invention provides a method and apparatus for the reduction of water content within an electrolytic capacitor casing to reduce degradation of the capacitor over time. According to the present invention, residual water in an electrolytic capacitor is reduced to an equilibrium level below 1% by weight of the electrolyte, to preferably about 0.75% by weight of the electrolyte, such that larger periods of inactivity between charging of the capacitor can be tolerated without degradation of the capacitor. Reformation of the barrier oxide layer formed on the anode foil of an electrolytic capacitor according to the present invention is required only after one month or more of inactivity.

Figure 3:
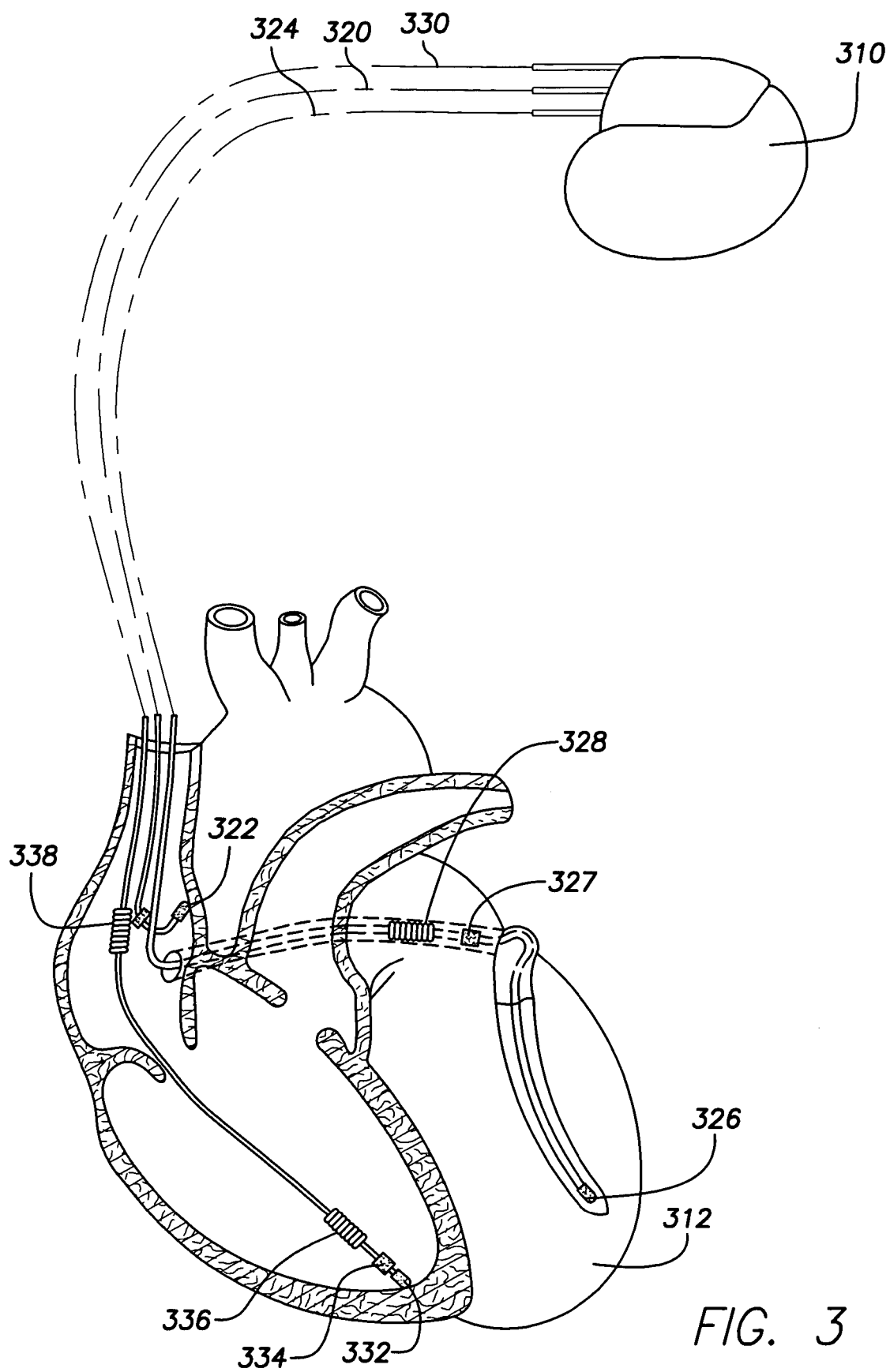
FIG. 3 is a simplified diagram illustrating an ICD according to the present invention in electrical communication with at least three leads implanted into a patient's heart for delivering multi-chamber stimulation and shock therapy.

Electrolytic capacitors according to the present invention are particularly useful in the environment of an implantable cardioverter defibrillator. As shown in FIG. 3, there is an exemplary ICD 310 in electrical communication with a patient's heart 312 by way of three leads, 320, 324 and 330, suitable for delivering multi-chamber stimulation and pacing therapy. As discussed below, an electrolytic capacitor according to the present invention can be used to store an electrical pulse just before delivery to the heart.

To sense atrial cardiac signals and to provide right atrial chamber stimulation therapy, ICD 310 is coupled to implantable right atrial lead 320 having at least an atrial tip electrode 322, which typically is implanted in the patient's right atrial appendage.

To sense left atrial and ventricular cardiac signals and to provide left-chamber pacing therapy, ICD 310 is coupled to "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

ICD 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, right ventricular lead 330 is transvenously inserted into heart 312 so as to place the right ventricular tip electrode 332 in the right ventricular apex so that RV coil electrode 336 will be positioned in the right ventricle and SVC coil electrode 338 will be positioned in the superior vena cava. Accordingly, right ventricular lead 330 is capable of receiving cardiac signals and delivering stimulation in the form of pacing and shock therapy to the right ventricle.

Figure 4:
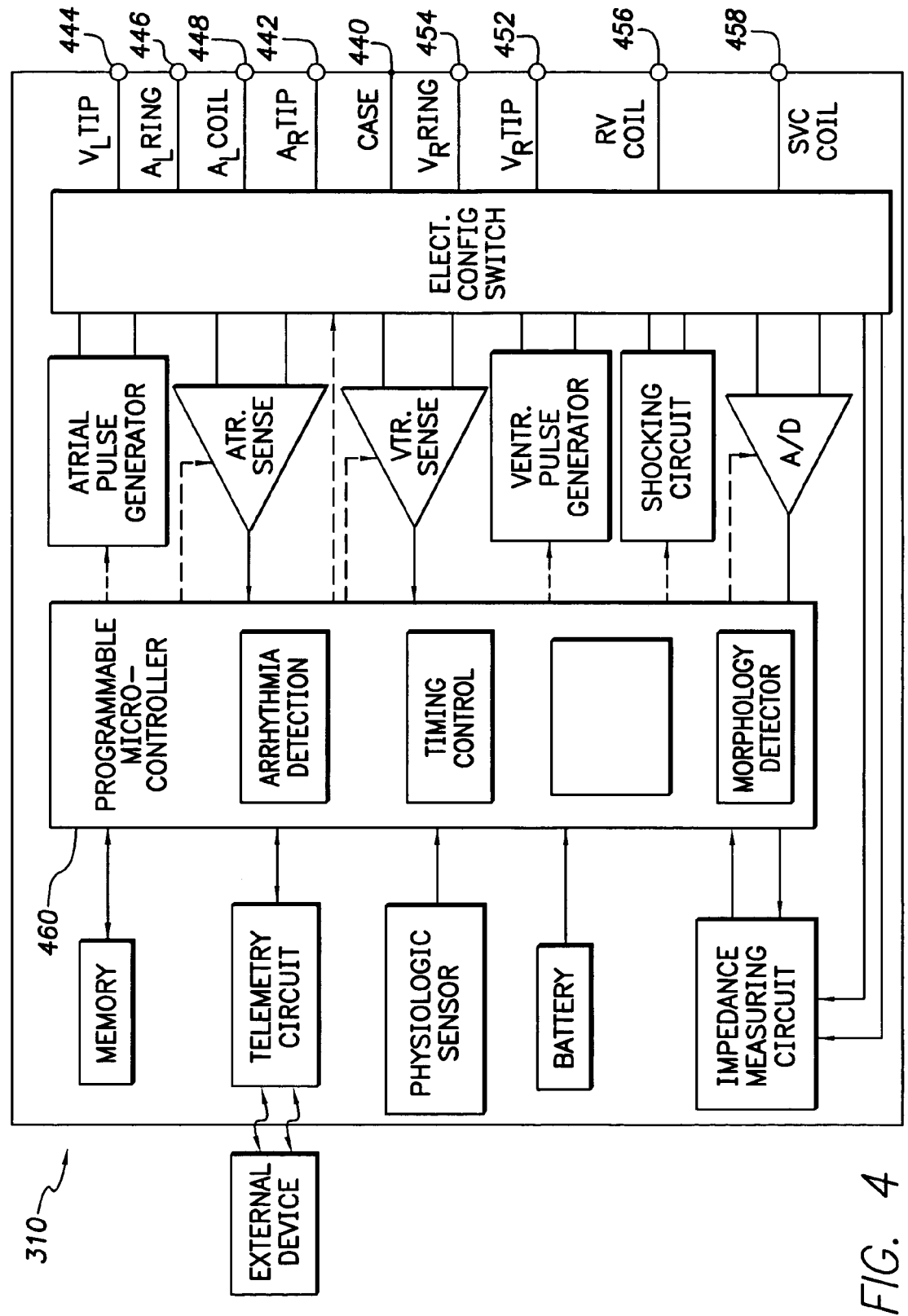
FIG. 4 is a functional block diagram of an ICD according to the present invention.

FIG. 4 is a simplified block diagram of ICD 310, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 440 of ICD 310, shown schematically in FIG. 4, is often referred to as the "can," "case" or "case electrode" and may be programmably selected to act as the return electrode for all "unipolar" modes. Housing 440 may further be used as a return electrode alone or in combination with one or more of coil electrodes, 328, 336, and 338 for shocking purposes. Housing 440 further includes a connector (not shown) having a plurality of terminals, 442, 444, 446, 448, 452, 454, 456, and 458 (shown schematically and, for convenience, the names of the electrodes to which they are connected are shown next to the terminals).

As such, to achieve right atrial sensing and pacing, the connector includes at least a right atrial tip terminal (AR TIP) 442 adapted for connection to atrial tip electrode 322. To achieve left chamber sensing, pacing and shocking, the connector includes at least a left ventricular tip terminal (VL TIP) 444, a left atrial ring terminal (AL RING) 446, and a left atrial shocking terminal (AL COIL) 448, which are adapted for connection to left ventricular ring electrode 326, left atrial tip electrode 327, and left atrial coil electrode 328, respectively. To support right chamber sensing, pacing, and shocking the connector also includes a right ventricular tip terminal (VR TIP) 452, a right ventricular ring terminal (VR RING) 454, a right ventricular shocking terminal (RV COIL) 456, and an SVC shocking terminal (SVC COIL) 458, which are configured for connection to right ventricular tip electrode 332, right ventricular ring electrode 334, RV coil electrode 336, and SVC coil electrode 338, respectively.

At the core of ICD 310 is a programmable microcontroller 460 which controls the various modes of stimulation therapy. As is known in the art, microcontroller 460 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 460 includes the ability to process or monitor input signals (data) as controlled by a program code stored in a designated block of memory. The details of the design of microcontroller 460 are not critical to the present invention. Rather, any suitable microcontroller 460 can be used to carry out the functions described herein. The use of microprocessor-based control circuits for performing timing and data analysis functions are known in the art.

Microcontroller 460 utilizes arrhythmia detection circuitry and morphology detection circuitry to recognize and classify arrhythmia so that appropriate therapy can be delivered. In the case where ICD 310 is intended to operate as a cardioverter, pacer or defibrillator, ICD 310 detects the occurrence of an arrhythmia and automatically applies an appropriate electrical therapy to the heart aimed at terminating the detected arrhythmia. To this end, microcontroller 460 incorporates charge control circuitry that controls a shocking circuit by way of control signals. The shocking circuit includes one or more high-voltage capacitors according to the present invention that are charged in response to control signals. The charge control circuitry senses the status of the shocking circuit via control signals and provides charge status information to microcontroller 460. Microcontroller 460, through timing control circuitry and charge control circuitry, controls charging of the shocking circuit.

The shocking circuit generates shocking pulses of low (up to 0.5 Joules), moderate (0.5–10 Joules), or high energy (11 to 40 Joules), as controlled by microcontroller 460. Such shocking pulses are applied to the patient's heart 312 through at least two shocking electrodes (e.g., selected from left atrial coil electrode 328, RV coil electrode 336, and SVC coil electrode 338). Housing 440 may act as an active electrode in combination with RV electrode 336, or as part of a split electrical vector using SVC coil electrode 338 or left atrial coil electrode 328 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, microcontroller 460 is capable of controlling the synchronous or asynchronous delivery of the shocking pulses.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A low deformation electrolytic capacitor, comprising:
   a housing;
   an anode disposed in said housing;

a barrier oxide layer formed on a surface of said anode;
a cathode disposed in said housing;
a separator material disposed between said anode and said cathode and impregnated with an electrolyte; and a desiccant material disposed in said housing, wherein the desiccant material reduces a portion of water inside the housing of the electrolytic capacitor.

2. An electrolytic capacitor according to claim 1, further comprising a moisture barrier layer covering said desiccant material.

3. An electrolytic capacitor according to claim 2, wherein said moisture barrier layer is a thin layer of parylene.

4. An electrolytic capacitor according to claim 2, wherein said moisture barrier layer is formed from the group of moisture barrier materials consisting of epoxies, silicones, urethanes and encapsulants.

5. An electrolytic capacitor according to claim 2, wherein said moisture barrier layer completely covers said desiccant material.

6. An electrolytic capacitor according to claim 1, wherein said desiccant material is adapted to reduce the water content inside said housing to below about 1% by weight of said electrolyte.

7. An electrolytic capacitor according to claim 6, wherein said desiccant material is capable of reducing the water content inside said housing to about 0.75% by weight of said electrolyte.

8. An electrolytic capacitor according to claim 1, wherein said desiccant material is applied to at least a portion of an inside surface of said housing.

9. An electrolytic capacitor according to claim 1, comprising about 5 mg to about 60 mg of said desiccant material.

10. An electrolytic capacitor according to claim 1, wherein said desiccant material is selected from the group consisting of silica gel, molecular sieve and clay.

11. An electrolytic capacitor according to claim 1, wherein said electrolytic capacitor comprises a multiple anode flat, stacked capacitor configuration.

12. An electrolytic capacitor according to claim 1, wherein said electrolytic capacitor comprises a wound roll configuration.

13. An electrolytic capacitor according to claim 1, wherein said anode is aluminum.

14. An electrolytic capacitor according to claim 13, wherein said barrier oxide layer is a thin film of aluminum oxide ($Al_2O_3$).

15. An electrolytic capacitor according to claim 1, wherein the initial water content inside said housing is about 2% to about 6% by weight of said electrolyte.

16. An implantable cardioverter defibrillator comprising a low deformation electrolytic capacitor, comprising:
a housing;
an anode disposed in said housing;
a barrier oxide layer formed on a surface of said anode;
a cathode disposed in said housing;
a separator material disposed between said anode and said cathode and impregnated with an electrolyte; and a desiccant material disposed in said housing, wherein the desiccant material reduces a portion of water inside the housing of the electrolytic capacitor.

17. A low deformation electrolytic capacitor, comprising:
a housing;
an anode disposed in said housing;
a barrier oxide layer formed on a surface of said anode;
a cathode disposed in said housing;
a separator material disposed between said anode and said cathode and impregnated with an electrolyte; and a desiccant material disposed in said housing; and a moisture barrier layer covering said desiccant material, the moisture barrier layer maintains a water content inside said housing for a predetermined period of time.

18. An electrolytic capacitor according to claim 17, wherein the water content inside said housing is about 2% to about 6% by weight of said electrolyte.

19. An electrolytic capacitor according to claim 18, wherein said desiccant material is adapted to reduce the water content inside said housing to below about 1% by weight of said electrolyte.

20. An electrolytic capacitor according to claim 19, wherein said desiccant material is adapted to reduce the water content inside said housing to about 0.75% by weight of said electrolyte.

21. An electrolytic capacitor according to claim 18, wherein said moisture barrier layer is formed from the group of moisture barrier materials consisting of epoxies, silicones, urethanes and encapsulants.

22. An electrolytic capacitor according to claim 17, wherein said desiccant material is selected from the group consisting of silica gel, molecular sieve and clay.

23. An electrolytic capacitor according to claim 17, wherein said moisture barrier layer is a thin layer of parylene.

* * * * *